United States Patent
Ankerhold

(12) 
(10) Patent No.: US 6,570,159 B2
(45) Date of Patent: May 27, 2003

(54) GAS-MEASURING SYSTEM

(75) Inventor: Georg Ankerhold, Lübeck (DE)

(73) Assignee: Drägerwerk Aktiengesellschaft (DE)

( * ) Notice: Subject to any disclaimer, the term of this patent is extended or adjusted under 35 U.S.C. 154(b) by 61 days.

(21) Appl. No.: 09/795,739

(22) Filed: Feb. 28, 2001

(65) Prior Publication Data

US 2001/0025927 A1 Oct. 4, 2001

(30) Foreign Application Priority Data

Mar. 29, 2000 (DE) .......................................... 100 15 615

(51) Int. Cl.[7] .............................................. G01N 21/35
(52) U.S. Cl. .............................. 250/338.5; 250/339.13; 356/437
(58) Field of Search ......................... 250/338.5, 339.13; 356/437

(56) References Cited

U.S. PATENT DOCUMENTS

| | | | | |
|---|---|---|---|---|
| 5,317,156 A | * | 5/1994 | Cooper et al. | 250/339.13 |
| 5,517,314 A | * | 5/1996 | Wallin | 250/252.1 |
| 5,767,976 A | * | 6/1998 | Ankerhold et al. | 250/338.5 |
| 6,137,817 A | * | 10/2000 | Baillargeon et al. | 356/437 |

FOREIGN PATENT DOCUMENTS

DE 19611290 C2 4/1998

* cited by examiner

*Primary Examiner*—Constantine Hannaher
(74) *Attorney, Agent, or Firm*—McGlew and Tuttle, P.C.

(57) ABSTRACT

An optical gas-measuring system and process identifies especially infrared-active individual gases over a measuring path of about 100 m and to determine their concentration averaged over the measuring path swept. The laser source (11) emits a divergent ray beam, from which both the measuring beam and the reference beam are formed after a single-time reflection of the emitted ray beam. A first radiation reflector (14) is designed in the form of a first hollow mirror for the reflection of a first part of the ray beam emitted from the laser source (11) as a measuring beam into the open optical measuring path. A second radiation reflector (16) is designed in the form of a second hollow mirror for the reflection of a second part of the ray beam emitted from the laser source (11) as a reference beam into a reference gas cuvette (17) containing the reference gas sample for the gas to be measured. A third radiation reflector (21) is designed in the form of a third hollow mirror for the reflection of the measuring beam received after passing through the optical measuring path onto a first radiation detector (22).

20 Claims, 1 Drawing Sheet

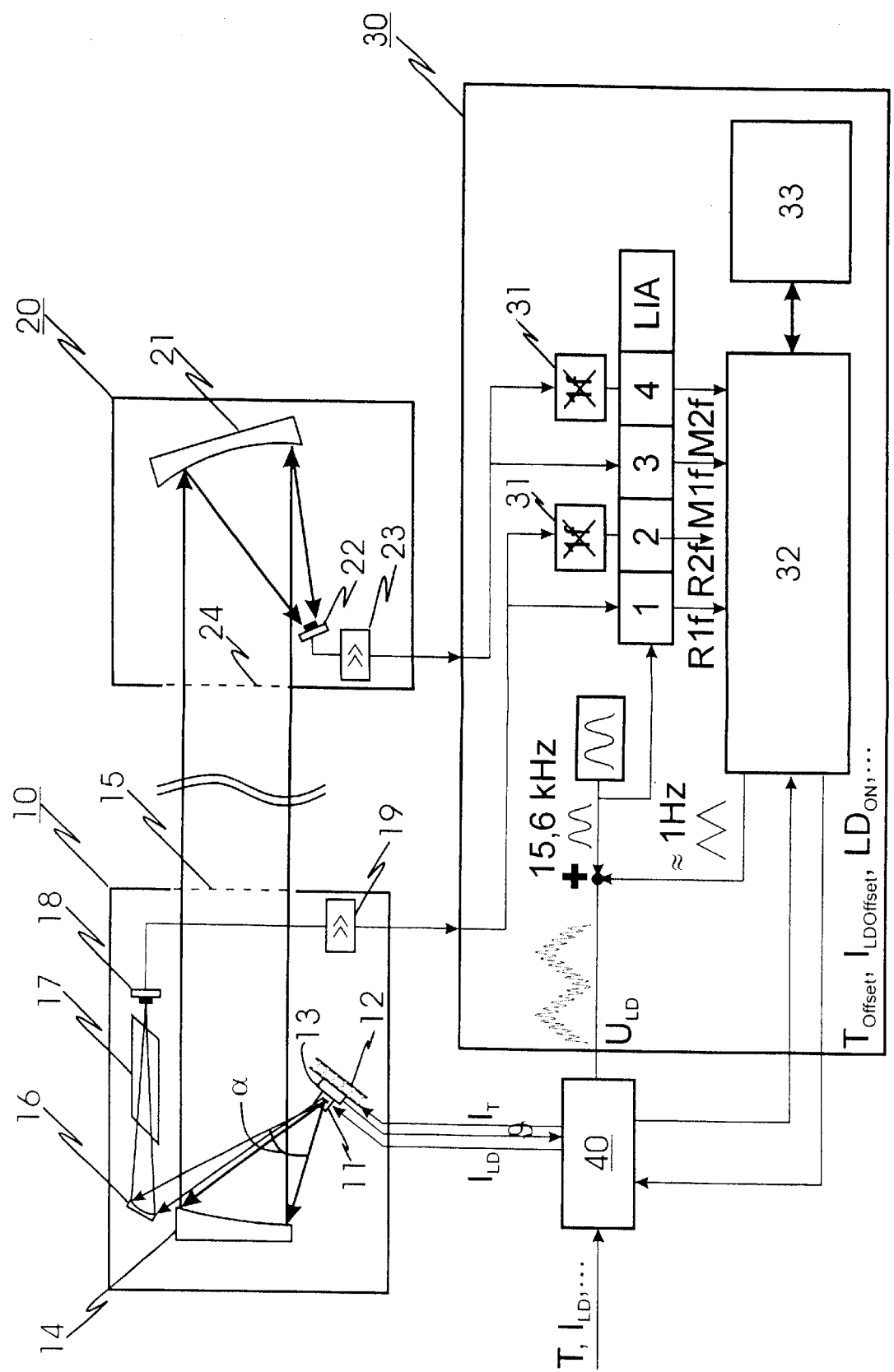

GAS-MEASURING SYSTEM

FIELD OF THE INVENTION

The present invention pertains to a gas-measuring system with an open optical measuring path for the spectroscopic measurement of at least one component of a gas sample with a laser source, a reference gas sample for the gas to be measured, two radiation detectors for the main beam and the reference beam and at least two radiation reflectors.

BACKGROUND OF THE INVENTION

A prior-art gas-measuring system of this type with an open optical measuring path (so-called open-path measurement) has been known from DE 196 11 290 C2 (and U.S. Pat. No. 5,767,976), wherein the transmitting and receiving optical systems are located close to one another in space and a retroreflector is additionally used. One essential drawback of this prior-art gas-measuring system is due to the interference with and the attenuation of the measured signal due to the beam passing through the necessary optical elements beam splitter and retroreflector. The optical path measurement of gases is, in general, the detection of trace amounts of gaseous substances which may be present at extremely low concentrations. The prerequisite for the optical quantification is, however, the presence of absorption bands of the gases to be detected in a spectral range accessible for the optical measuring technique being used. To reach a low detection limit, a spectral range is expediently selected in which the gas to be analyzed has a pronounced infrared activity, i.e., intense optical absorption, and in which the lowest possible cross sensitivities, especially with atmospheric gases such as water or carbon dioxide, prevail. An intense optical absorption by gas molecules usually takes place in the spectral range of the principal molecular vibrations, which are often in one of the two wavelength ranges of 2 to 5 micrometer ($\mu$m) and 8 to 12 micrometer ($\mu$m). On the other hand, the prior-art optical arrangements and radiation sources are characterized by relatively poor received measured signal quality, which is due especially to the radiation sources used in combination with the optical elements used.

SUMMARY AND OBJECTS OF THE INVENTION

The object of the present invention is to provide an improved gas-measuring system of the type mentioned in the introduction with an open optical measuring path without a retroreflector, which does not make it necessary to use a beam splitter.

According to the invention, a gas-measuring system is provided with an open optical measuring path for the spectroscopic measurement of at least one component of a gas sample with a laser source, a reference gas sample for the gas to be measured, two radiation detectors for the main beam and the reference beam and at least two radiation reflectors. The laser source is provided to emit a divergent ray beam, from which both the measuring beam and the reference beam are formed after a single-time reflection of the emitted ray beam. A first radiation reflector is provided in the form of a first concave mirror for the reflection of a first part of the ray beam emitted from the laser source as a measuring beam into the open optical measuring path. A second radiation reflector is provided in the form of a second concave mirror for the reflection of a second part of the ray beam emitted from the laser source as a reference beam into a reference gas cuvette containing the reference gas sample for the gas to be measured. A third radiation reflector is provided in the form of a third concave mirror for the reflection of the measuring beam received after passing through the optical measuring path onto a first radiation detector.

The first radiation reflector may be a paraboloidal mirror designed as an asymmetric mirror in relation to the optical axis. The second radiation reflector may be designed as a spherical mirror or a paraboloidal mirror.

The laser source may be a near infrared laser diode or a quantum cascade laser. The optical measuring path may advantageously be 1 to 200 meters (m).

According to a further aspect of the invention, a process is provided including using the system as described above for detecting one or more of the gases hydrogen sulfide ($H_2S$), ammonia ($NH_3$), hydrochloric acid (HCl), phosgene ($COCl_2$), carbon monoxide (CO), and methane ($CH_4$).

One essential advantage of the present invention arises from the use of very few optical elements, so that disturbances and loss of intensity of the measuring beam are extensively avoided. The object is accomplished especially by a first radiation reflector being designed in the form of a concave mirror and especially preferably in the form of a paraboloidal mirror which is asymmetric in relation to the optical axis, a so-called off-axis paraboloidal mirror, so that the divergent ray beam emitted by the laser source sweeps both this first radiation reflector and a second radiation reflector arranged in the vicinity, which is in the form of a concave mirror and preferably in the form of a spherical mirror or paraboloidal mirror, in a specific manner. The ray beam emitted by the first radiation reflector forms the measuring beam, which reaches a first radiation detector after passing through the measuring path via a third radiation reflector. The ray beam reflected by the second radiation reflector is used as a reference beam and is directed toward a second radiation detector via a reference gas cuvette containing a reference gas sample of the gas to be measured.

An especially preferred laser source is a quantum cascade laser, which emits a pulsating radiation and with which the optical wavelength range of 2 to 12 micrometers ($\mu$m) of the near to middle infrared range, which is of particular interest, can be covered.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

BRIEF DESCRIPTION OF THE DRAWINGS

In the drawings:

The only FIGURE is a schematic view of a gas-measuring system according to the present invention.

DESCRIPTION OF THE PREFERRED EMBODIMENTS

Referring to the drawings in particular, the only FIGURE schematically shows a gas-measuring system according to the present invention. The gas-measuring system according to the present invention comprises the functional units optical transmitter arrangement 10, the optical receiving arrangement 20, the evaluating arrangement 30, and the laser control device 40 for the power and temperature control of the laser source 11. The laser source 11 is located on a thermoelectric Peltier cooling element 12, together with a temperature sensor 13.

The laser source 11 is preferably a quantum cascade laser emitting a pulsating radiation in the near to middle infrared or a commercially available laser diode, which is used in the exemplary embodiment and emits radiation continuously in the near infrared in continuous operation and emits a greatly divergent ray beam with an opening angle α of about 35° in the example. The first radiation reflector 14, which is preferably designed as a paraboloidal mirror that is asymmetric in relation to the optical axis, and the second radiation reflector 16, which is preferably designed as a spherical mirror or a paraboloidal mirror, are arranged, as is shown, so close to one another that the ray beam emitted by the laser source 11 irradiates both the first radiation reflector 14 and the second radiation reflector 16, so that a hitherto usual beam splitter for splitting the ray beam into a measuring beam and a reference beam becomes unnecessary.

The first radiation reflector 14 is used to collimate the measuring beam of the divergent ray beam from the laser source 11, which first passes through a first foil window 15 over the open path and subsequently through a second foil window 24 to enter the receiving arrangement 20. There, the measuring beam falls on a third radiation reflector 21 and is finally focused on a first radiation detector 22 with a downstream pre-amplifier 23.

The evaluation of the amplified measured signals takes place in the evaluating arrangement 30.

A second part of the ray beam from the laser source 11, namely, the reference beam, first reaches the second radiation reflector 16, which focuses the radiation via a reference gas cuvette 17 with the reference gas sample of the gas to be measured on a second radiation detector 18 with a downstream pre-amplifier 19. The amplified measured signals are likewise sent to the evaluating arrangement 30. The measured signals are subjected to phase-sensitive evaluation in the evaluating arrangement 30 according to known methods, and the first harmonics are excluded by means of suitable filters 31. The measurement results are passed on to an input and display unit 33 via a data acquisition unit 32 and input values are processed in the gas-measuring system. The laser source 11 is modulated by means of the laser control device 40 and the evaluated measured signals.

If a quantum cascade laser emitting pulsed infrared radiation with a pulse width of up to several 100 nanoseconds and pulse repetition rates of up to several megahertz is used as the laser source 11 in conjunction with a correspondingly modified laser control device 40, the evaluation can take place in the evaluating arrangement 30 in a similarly phase-sensitive manner as in the case of the use of modulated, but continuously emitting laser diodes. One can also speak of quasi-continuous laser radiation in the case of quantum cascade lasers due to the high pulse repetition rates in the megahertz range compared with the low modulation frequencies of a few kilohertz, so that the individual, short laser pulse no longer needs to be resolved in time during the detection at the two radiation detectors 18 and 22.

The invention further comprises the use of one of the embodiments of the system as described herein as part of a process for detecting the gases hydrogen sulfide ($H_2S$), ammonia ($NH_3$), hydrochloric acid (HCl) and methane ($CH_4$). The system provides particularly good results for such detection.

While specific embodiments of the invention have been shown and described in detail to illustrate the application of the principles of the invention, it will be understood that the invention may be embodied otherwise without departing from such principles.

What is claimed is:

1. A gas-measuring system with an open optical measuring path for the spectroscopic measurement of at least one component of a gas sample, the system comprising:

an optical transmission arrangement having a laser source for emitting a divergent ray beam, a reference gas sample space, a reference beam radiation detector for detection of a reference beam directed through the reference gas sample space, a first radiation reflector with a first concave mirror for the reflection of a first part of the ray beam emitted from the laser source to form a measuring beam directed into a space of the open optical measuring path, a second radiation reflector with a second concave mirror for the reflection of a second part of the ray beam emitted from the laser source as the reference beam into said reference gas sample space and onto said reference beam radiation detector; and an optical receiving arrangement positioned relative to the optical transmission arrangement to form an open path measuring distance, the optical receiving arrangement having a first radiation detector for the measuring beam and a third radiation reflector with a third concave mirror for the reflection of the measuring beam received after passing through the open path measuring distance onto said first radiation detector.

2. A gas-measuring system in accordance with claim 1, wherein the first radiation reflector is a paraboloidal mirror, asymmetric in relation to an optical axis thereof.

3. A gas-measuring system in accordance with claim 1, wherein said second radiation reflector is a spherical mirror or a paraboloid mirror.

4. A gas-measuring system in accordance with claim 1, wherein the first radiation reflector is a paraboloid mirror, asymmetric in relation to an optical axis thereof and wherein said second radiation reflector is a spherical mirror or a paraboloid mirror.

5. A gas-measuring system in accordance with claim 1, wherein the laser source is a near infrared laser diode or a quantum cascade laser.

6. A gas-measuring system in accordance with claim 1, wherein the optical measuring path is 1 to 200 meters.

7. A gas-measuring system in accordance with claim 1, wherein the first radiation reflector and the second radiation reflector are on one side of the laser source.

8. A gas-measuring system in accordance with claim 1, wherein the measuring beam and the reference beam extend on one side of the laser source and the divergent ray beam.

9. A gas-measuring system in accordance with claim 1, wherein the divergent ray beam is formed with a laser source having an opening angle of about 35°.

10. A gas-measuring system in accordance with claim 1, wherein the measuring beam and the reference beam are substantially equal in intensity to the intensity of the divergent ray beam.

11. A process for spectroscopic measurement of at least one component of a gas sample with an open optical measuring path extending therethrough, the process comprising the steps of:

providing an optical transmission arrangement having a reference gas sample space, a reference beam radiation detector for detection of a reference beam directed through the reference gas sample space, a first concave mirror, a second concave mirror;

providing an optical receiving arrangement having a first radiation detector for a measuring beam and a third concave mirror;

positioning the optical transmission arrangement relative to the optical receiving arrangement to define an open path measuring distance;

using a laser source to emit a divergent ray beam at the optical transmission arrangement directed toward the first concave mirror and the second concave mirror;

reflecting a first part of the ray beam emitted from the laser source as the measuring beam into the open optical measuring path with the first concave mirror;

reflecting a second part of the ray beam emitted from the laser source as the reference beam into the reference gas sample and onto the reference radiation detector with the second concave mirror disposed adjacent to the first concave mirror as part of the optical transmission arrangement; and reflecting the measuring beam received at the optical receiving arrangement, after the measuring beam passes through the open path measuring distance, onto the measurement radiation detector using the third concave mirror at the optical receiving arrangement.

12. A process for spectroscopic measurement of at least one component of a gas sample according to claim 11, further comprising:

detecting one or more of the gases hydrogen sulfide ($H_2S$), ammonia ($NH_3$), hydrochloric acid (HCl), phosgene ($COCl_2$), carbon monoxide (CO), and methane ($CH_4$).

13. A process for spectroscopic measurement of at least one component of a gas sample according to claim 11, wherein the first concave mirror is a paraboloidal mirror that is asymmetric in relation to an optical axis thereof.

14. A process for spectroscopic measurement of at least one component of a gas sample according to claim 13, wherein the measuring beam and the reference beam extend on one side of the laser source and the divergent ray beam.

15. A process for spectroscopic measurement of at least one component of a gas sample according to claim 13, wherein the measuring beam and the reference beam are substantially equal in intensity to the intensity of the divergent ray beam.

16. An open path measuring device for the spectroscopic measurement of at least one component of a gas sample in an open path measuring space, the device comprising:

an optical transmission unit having
a laser source for emitting a divergent ray beam;
a reference gas sample space;
a reference beam radiation detector for detection of a reference beam directed through the reference gas sample space;
a first radiation reflector with a first concave mirror for the reflection of a first part of the ray beam emitted from the laser source to form a measuring beam directed into the open path measuring space, the first concave mirror having a reflection surface that is a portion of a paraboloid with an optical axis, said surface that is a portion of a paraboloid being asymmetric in relation to an optical axis thereof;
a second radiation reflector with a second reflector concave mirror for the reflection of a second part of the ray beam emitted from the laser source as the reference beam into said reference gas sample space and onto said reference beam radiation detector wherein the measuring beam and the reference beam are substantially equal in intensity to the intensity of the divergent ray beam; and an optical receiving unit separated from said optical transmission unit by the open path measuring space having
a first radiation detector for a measuring beam
a third radiation reflector with a third concave mirror for the reflection of the measuring beam received after passing through the optical measuring path space onto said first radiation detector.

17. A device in accordance with claim 16, wherein the first radiation reflector and the second radiation reflector are on one side of the laser source.

18. A device in accordance with claim 16, wherein the measuring beam and the reference beam extend on one side of the laser source and the divergent ray beam.

19. A device in accordance with claim 16, wherein the first concave mirror is a paraboloidal producing the reference beam with substantially parallel rays.

20. A device in accordance with claim 16, wherein the divergent ray beam is formed with a laser source having an opening angle of about 35°.

* * * * *